United States Patent
Bankers et al.

(10) Patent No.: US 7,793,860 B2
(45) Date of Patent: *Sep. 14, 2010

(54) PISTON ACTUATED VAPOR-DISPERSING DEVICE

(75) Inventors: Jeffrey Bankers, Phoenix, AZ (US); Kevin Hafer, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 649 days.

This patent is subject to a terminal disclaimer.

(21) Appl. No.: 11/654,440

(22) Filed: Jan. 17, 2007

(65) Prior Publication Data

US 2008/0169306 A1    Jul. 17, 2008

(51) Int. Cl.
| | |
|---|---|
| A24F 25/00 | (2006.01) |
| A61L 9/04 | (2006.01) |
| B67D 7/08 | (2010.01) |
| B05B 1/08 | (2006.01) |
| B05B 9/00 | (2006.01) |
| A62C 13/62 | (2006.01) |
| B65D 69/00 | (2006.01) |
| B65D 85/00 | (2006.01) |
| B67B 7/00 | (2006.01) |
| B67D 7/00 | (2010.01) |
| B65B 53/00 | (2006.01) |

(52) U.S. Cl. .............. 239/50; 239/6; 239/44; 239/72; 239/73; 239/102.1; 239/102.2; 239/51.5; 239/56; 239/302; 239/326; 206/223; 206/525; 222/1; 222/3; 428/34.9

(58) Field of Classification Search .............. 239/44, 239/6, 72, 733, 102.1, 102.2, 274, 47, 51.5, 239/57, 145, 302, 326, 70, 68, 69, 45, 50, 239/56; 206/525, 223; 222/1, 3; 428/34.9
See application file for complete search history.

(56) References Cited

U.S. PATENT DOCUMENTS

| | | | | |
|---|---|---|---|---|
| 2,608,436 | A | * | 8/1952 | Baughman .................. 239/47 |
| 4,059,227 | A | * | 11/1977 | Hunter ......................... 239/1 |
| 4,477,414 | A | | 10/1984 | Muramoto et al. |
| 4,869,407 | A | | 9/1989 | Booth, Jr. et al. |
| 4,946,100 | A | * | 8/1990 | Flemming et al. .............. 239/1 |
| 5,221,025 | A | * | 6/1993 | Privas .......................... 222/1 |
| 5,447,273 | A | * | 9/1995 | Wozniak ...................... 239/70 |
| 5,449,117 | A | * | 9/1995 | Muderlak et al. ............... 239/6 |
| 5,515,842 | A | * | 5/1996 | Ramseyer et al. ......... 128/200.18 |
| 5,776,561 | A | | 7/1998 | Lindauer |
| 5,954,268 | A | | 9/1999 | Joshi et al. |
| 5,970,974 | A | * | 10/1999 | Van Der Linden et al. ..................... 128/200.16 |
| 6,223,746 | B1 | * | 5/2001 | Jewett et al. ........... 128/203.12 |
| 6,264,548 | B1 | * | 7/2001 | Payne et al. .................. 454/157 |
| 6,267,297 | B1 | * | 7/2001 | Contadini et al. .............. 239/1 |
| 6,595,208 | B1 | * | 7/2003 | Coffee et al. ........... 128/203.12 |
| 6,655,604 | B2 | * | 12/2003 | Tuttobene, Jr. ................. 239/6 |
| 6,827,286 | B2 | * | 12/2004 | Zobele ........................ 239/44 |
| 6,923,383 | B1 | | 8/2005 | Joshi et al. |
| 2003/0235522 | A1 | | 12/2003 | Harrop et al. |
| 2004/0021001 | A1 | * | 2/2004 | Zobele ........................ 239/44 |
| 2006/0261179 | A1 | * | 11/2006 | Davies et al. ................. 239/34 |

\* cited by examiner

*Primary Examiner*—Len Tran
*Assistant Examiner*—Steven M Cernoch
(74) *Attorney, Agent, or Firm*—Paul A. Pappalardo

(57) ABSTRACT

A vapor-dispersing device comprising a moveable piston with a porous protuberance is described that operates by the repetitive movement of the piston to intermittently dip the porous member into a volatile liquid and to expel air out through vents.

20 Claims, 9 Drawing Sheets

PISTON ACTUATED VAPOR-DISPERSING DEVICE

FIELD OF INVENTION

The present invention relates to electromechanical vapor-dispersing devices and in particular to a vapor-dispersing device with a moveable piston that repeatedly dips a porous member into a volatile liquid to draw up the liquid from a reservoir and to move the air around the porous member creating a bellows effect that evaporates the volatile liquid from the device into the adjacent environment in a linear and controlled manner.

BACKGROUND

Vapor-dispersing devices are well known and include a variety of devices for vaporizing a liquid such as a perfume or insecticide into the surrounding environment. For example, vapor-dispersing devices include electrical devices with resistive heater modules and/or fans for driving liquids into the vapor phase, passive devices that rely on pads or wicks with large surface area for evaporating liquids without energy input, and simple aerosol sprays that propel and disperse liquids into fine droplets that evaporate in the air. Vapor-dispersing devices that are electrically powered are very common in home and institutional settings around the world. These devices may comprise a bottle of volatile liquid and they may operate by heat to volatize the liquid. Most common of these devices are air fresheners wherein a porous plastic wick is in communication with a bottle of scented fragrance oil and wherein the wick, continuously saturated with the fragrance, is placed in close proximity to a resistive heater element that accelerates the evaporation of the liquid from the wick. Another common configuration for a household air freshener comprises a bottle of scented fragrance oil with a porous plastic wick positioned in front of a fan. In these devices the fan moves air across the wick and the scented air is expelled into the immediate environment. These devices exist in the marketplace, both house current (110 v/220 v, AC) powered and battery powered (1.5 v, 3 v, 9 v, etc., DC). Exemplary devices include the Glade® Plugins® Scented Oil and Plugins® Scented Oil Fan air freshener products from S.C. Johnson & Son, Inc., and the Mobil'Air® Portable Electric Diffuser air freshener from Reckitt Benckiser. More elaborate products include piezoelectric devices wherein the scented fragrance oil is wicked up from a reservoir onto a vibrating plate where it is expelled into very fine droplets that quickly evaporate. One such device is the battery operated Glade® Wisp® Scented Oil Fragrancer air freshener from S.C. Johnson & Son.

In spite of the fact that fan, heater and piezoelectric air fresheners have dominated the marketplace over the last decade or so, there remain many limitations to such devices. Most problems relate to the fact that the wick remains in constant communication with the volatile liquid, and remaining continually saturated there is separation of fragrance components through what is nothing more than column chromatography. Invariably these devices slow down since the porous wicks clog with the less volatile ingredients and the spectrum of fragrance notes changes throughout the lifetime of the device.

We have invented a unique way to circumvent these limitations by keeping the porous member out from constant contact with the volatile liquid and keeping it from complete saturation. The way the present invention accomplishes this is by having a moveable piston that carries the porous member repeatedly into and out of the volatile liquid with each stroke. By changing from constant contact of the wick with the volatile liquid to repeated dipping, the evaporation of the liquid is more controlled and the distribution of the volatile components remains more constant throughout the evaporation of the liquid. The movement of the piston also serves as a bellow-means to expel the air treated with the volatile material into the environment.

Vapor-dispersing devices that contain pistons are extremely scant in the literature and are all based on movement of a piston to increase internal pressure within a reservoir to push liquid out. For example, U.S. Pat. No. 5,954,268 to Joshi, et al. and U.S. Pat. No. 5,776,561 to Lindauer both describe reservoirs that may be pressurized by depression of a piston and wherein the pressure forces liquid fragrance up a capillary tube and out onto an evaporative surface formed in the shape of a decorative flower.

U.S. Pat. No. 4,477,414 to Muramoto, et al. describes a piston operable device where depression of the piston forces liquid out through a capillary tube and onto an impregnation member where it evaporates. U.S. Pat. No. 6,923,383 to Joshi, et al. describes a device wherein a piston-actuated pressurization expels liquid through a restrictive opening. Lastly, piston actuated spray devices include the device described in U.S. Pat. No. 5,221,025 to Privas.

Devices that employ a bellows-type action to expel scented air include the devices described in U.S. Pat. No. 4,869,407 to Booth, et al.

None of these devices employ a moveable piston in a non-pressurized device for effecting the repeated dipping of a porous member into a volatile liquid so that the liquid is evaporated into the environment in a controlled manner.

SUMMARY OF THE INVENTION

It has now been discovered that placing the porous member in motion allows for the intermittent dipping of a porous member into a volatile liquid as a way to smooth out delivery of the volatile liquid over time.

For example, the present invention relates to a device that minimally comprises a housing with a vent for air exchange, a movable piston with an attached porous member as a protuberance to the piston, a reservoir with a breachable opening containing the volatile liquid, an electromechanical means to move the piston, a drive means connecting the piston with the electromechanical means, and an electrical means to power and control the electromechanical means and hence the piston, embodiments of which are encompassed in the following drawing figures. The invention also provides a previously unheard of method for evaporating a liquid that involves repetitive dipping of a porous member into a volatile liquid.

DETAILED DESCRIPTION OF THE INVENTION

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function, the size, and arrangement of the elements described without departing from the scope of the invention as set forth in the appended claims. Most importantly, changes in shape and size of the overall device do not depart from the intended scope of the invention.

That said, the present invention relates to a piston-actuated electromechanical vapor-dispersing device that shows a more linear evaporation of volatile liquid than conventional electrical devices utilizing heater and/or fan elements.

The present invention relates to a device that minimally comprises a housing with an air vent, a movable piston with an attached porous member as a protuberance to the piston, a reservoir with a breachable opening containing the volatile liquid, an electromechanical means and drive means to move the piston in repetitive strokes, and an electrical means to power and control the electromechanical means and hence the piston. In the simplest embodiment, the piston moves in a stroke range somewhere between the confines of an extreme lower position where the porous protuberance has pushed through the breachable opening of the reservoir and is pressed to the bottom of the reservoir and into the volatile liquid, to an extreme upper position where the porous protuberance is retracted fully from the reservoir to as high as the electromechanical and drive means and the housing length will allow. Between these two extreme positions, the piston moves along a path within a housing to bring the porous protuberance repeatedly into the volatile liquid and past at least one vent, and to provide air movement around the porous material and out to the environment to effectively evaporate the liquid. The repeated stroke of the piston provides a bellows effect that facilitates exchange of air within the device and movement of vapor from the interior of the device to the surrounding environment.

Figure 1:
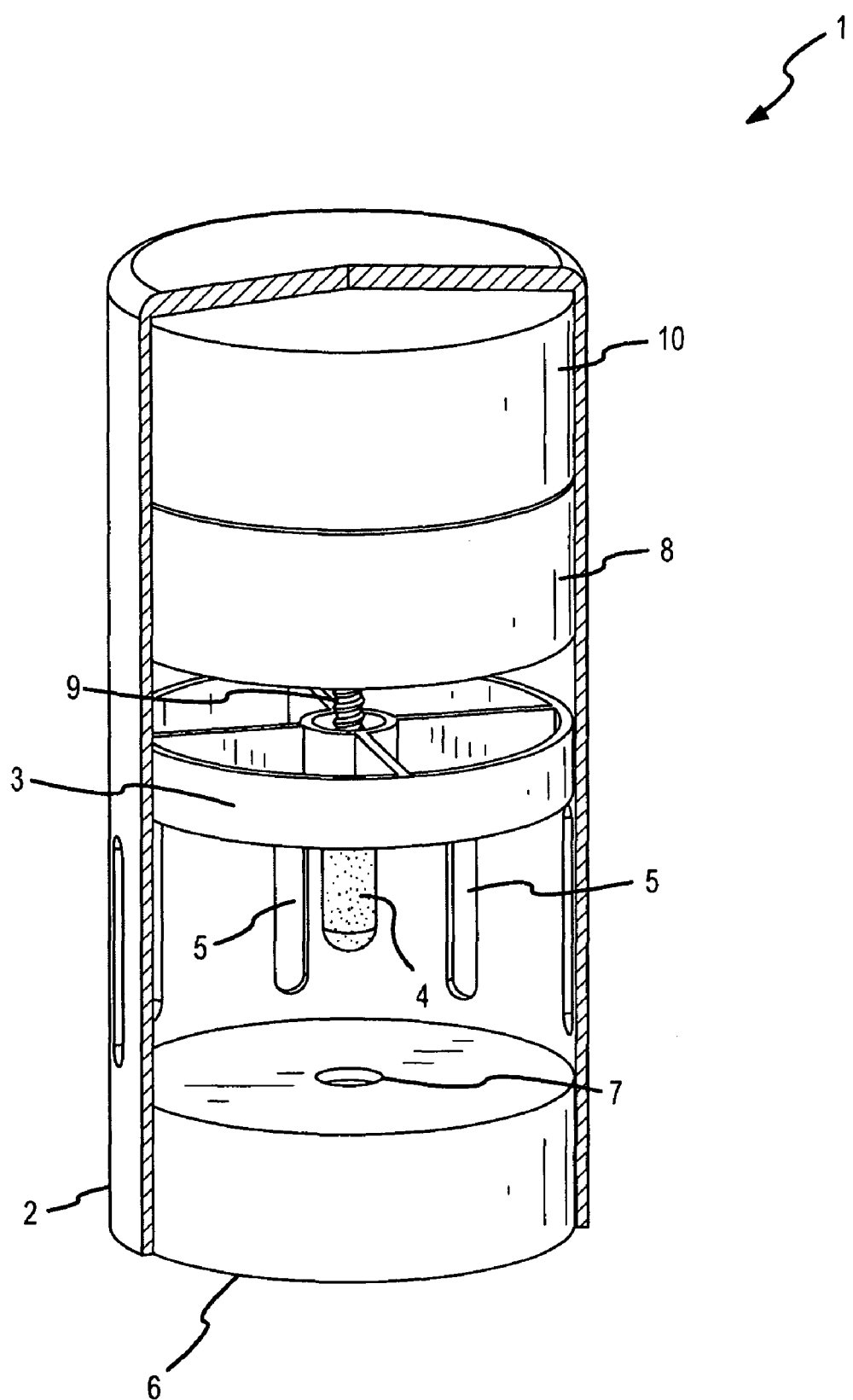
FIG. 1 conceptually outlines one embodiment of the vapor-dispersing device of the present invention with the movable piston in a one position.

Referring now to FIG. 1, one embodiment of the vapor-dispersing device 1 of the present invention comprises housing 2, moveable piston 3, porous member 4, air vent 5, reservoir 6, breachable opening 7, electromechanical means 8, drive means 9, and electrical control means 10. The size of the overall device 1 may be any size practical to maintain function and portability. It may be miniaturized, just a few inches in height and width, or the device may be quite large, as large as 12 inches or more in height and in width. A smaller dimensioned device may be used to treat a small room with volatized material such as an insecticide or fragrance, whereas a large unit may be used in institutional and industrial settings to disperse large amounts of vaporized material into much larger spaces including outdoor areas. The device 1 may sit on a surface, such as a floor, table or a shelf in a home or office, or it may be mounted to a wall or to a ceiling or plugged directly into an electrical outlet for support. It may be placed out of sight, for example inside of HVAC air ductwork, or it may be placed outdoors. It may be decorative and displayable or it may be utilitarian in appearance and hidden from view when in use. Depending on the configuration of the individual elements and the nature of the volatile liquid, the device need not be operated in a vertical position with the reservoir at the bottom end of the device. Some embodiments of the present invention may be operated in a position inverted from that shown in FIG. 1, or lying down or really in any other position.

The housing 2 defines the overall shape of the device 1. The housing may be comprised of any suitable material such as metal, plastic, glass or fiberboard, or combinations thereof. It may be cylindrical, cubic or rectangular in shape. Although any shape is theoretically possible, a cylindrical shape is preferred for simplicity of fitting a moveable piston inside (explained below). A preferred embodiment is to have a molded plastic or fiberboard cylinder, i.e. a tube, defining the sidewalls of the housing, with other components (detailed below) pressed into each end of the housing to close off both top and bottom ends. Overall, the housing 2 is a container with top, bottom and sidewalls that define an interior space. Most preferred is a cylinder shaped housing 2 with dimensions of from about 1.5 to about 8 inches in height and from about 0.5 to about 4 inches in diameter.

Also depicted in the embodiment of FIG. 1 is the vent 5 on the housing 2. It must be stressed that the size, shape, and number of vents is entirely variable. There may be one vent 5, or there may be many in the housing. The number and size of the vents are chosen such that the rate of evaporation of the volatile liquid within the device conforms to the application and the consumer needs. For example, if the device 1 is embodied as an air freshener, the vents on the device may be designed such that the supply of fragrance inside is evaporated to the environment in a reasonable time such as over a 30-90 day period. If the device is embodied as an insecticide disperser, then the vents in the device may be designed for another rate of delivery of the volatile liquid or fashioned to allow passageways for insects to move in and out of the device. The vent or vents 5 on the housing are essentially "holes" that allow the exchange of air between the inside and outside of the housing. The device is designed to transfer liquid from the inside of the device to vapor in the environment outside of the device, and thus the vent or vents are what make the movement of vapor to the outside of the device possible. Ideally the vent or vents are sized such that a child's finger cannot be inserted through it or them, for example smaller than 0.5 inches in diameter if round and unguarded. Otherwise the vent or vents may be screened in with mesh (plastic, metal, etc.), or an entire section of the housing may be constructed of mesh or screen and this grill area becomes the vent or vents. The vent or vents are positioned on the housing such that the movement of the piston within the housing moves air through them. The vent 5 may include adjustment means, such as moveable louvers or windows that allow control over the size of the openings in the device. One such embodiment may be to have concentric cylindrical tubes as the housing whereby rotation of the outer tube in relation to the inner tube opens and closes the vents 5. The vent or vents 5 may add to the overall décor of the device and can take on any decorative shape and arrangement for this purpose. Similarly any screening over the vents may be decorative or utilitarian.

Continuing with FIG. 1, an additional essential element of the present invention is a moveable piston 3 within the housing 2. The moveable piston is dimensioned to fit the interior of the housing such that there is little resistance to movement along the interior length of the housing and a reasonably close fit to the interior walls of the housing such that the piston may pull in ambient air and push out vapors through the vent or vents described above with each stroke. The piston necessarily comprises a top and bottom, along with sidewalls, wherein the sidewalls define the thickness between the top and bottom. The most preferred configuration for the moveable piston is disc-shaped such that it may fit the preferred cylindrical shape for the housing, and in this particular embodiment the piston would comprise a top and bottom and a sidewall having a circumference that reasonably matches the inside circumference of the housing. If a rectangular or square shaped housing were utilized, then the moveable piston would necessarily be configured to a rectangular or square shape, respectively. The thickness of the piston (determined by the height of the sidewalls mentioned) may be quite variable, but for practical and cost reasons the height/thickness is preferentially from about 0.125 inches to about 2 inches. The most preferred dimensions for a disc-shaped piston is a diameter of from about 0.5 to about 4 inches and a height/thickness of from about 0.25 to about 1 inch. The preferred material of construction for the moveable piston 3 is injection molded or thermoformed plastic, although other materials such as wood, metal, porous plastic, ceramic or fiberboard, or combinations of any of these materials are within the scope of the present invention. The piston may be constructed of one continuous part or it may be an assembly of more than one part glued or sonically welded together. Most preferred is to utilize an injection molded, disc-shaped plastic piston that has two axially opposed recesses, one molded or post-drilled into the top and one molded or post-drilled into the bottom of the piston. It is preferred that either the top or the bottom of the piston comprise a relatively planar and solid faceplate (i.e., a solid surface), such that the piston will move air during each stroke. A preferred embodiment for the piston is a two-piece assembly, wherein the first part preferably comprises a molded plastic wheel shape with spokes and wherein a second piece comprises a flat doughnut or washer constructed of plastic, fiberboard or paper, each part having the same diameter, and wherein the completed piston is comprised of the two pieces glued or welded together. It is preferable that both of the parts be molded of plastic, and the assembly thereby will be a disc-shaped piston with axially opposing recesses on the top and the bottom and either the top or the bottom including a relatively flat, solid faceplate to ensure that the piston can move air.

Also essential to the present invention and depicted in FIG. 1 is the porous member 4, configured as a protuberance from the piston 3. The porous member 4 is preferentially press-fit into a recess molded or post-drilled into either the top or bottom of the piston 3, however it is possible, though expensive, to mold a one-piece porous plastic piston with a protuberance and in this way the entire piston is porous and amenable to wetting with volatile liquid. The porous member may be simply attached to either the top or bottom of the piston by adhesives or with fasteners such as screws or rivets, or it may have a threaded end that screws into a threaded recess on the piston, or as mentioned may be press fit into a hole. The preferred porous member is a porous plastic wick similar to those found in household electric "plug-in" scented oil air fresheners. Such porous plastic materials are described in U.S. Patent Application Publication US2005/0191481 and the preferred porosities (pore size and void volumes) and sintered plastics are incorporated herein by reference. The porous member may also be comprised of cellulose or plastic fibers, ceramics, wood or graphite. The dimensions of the porous member may be from about 0.125 to about 1 inch in width and from about 0.25 to about 4 inches in length. The porous member may be rod-shaped, half-spherical, or rectangular (stick-shaped) so long as it protrudes at least somewhat from either the top or bottom of the piston. Most preferred is a molded sintered porous plastic wick in a rod-shape having dimensions of from about 0.125 to about 0.5 inches in diameter and from about 0.25 to about 3 inches in length. Most preferred is to press-fit this rod-shaped molded porous plastic wick into an appropriately dimensioned recess molded or post-drilled into either the top or the bottom of an injection-molded plastic moveable piston.

Figure 7:
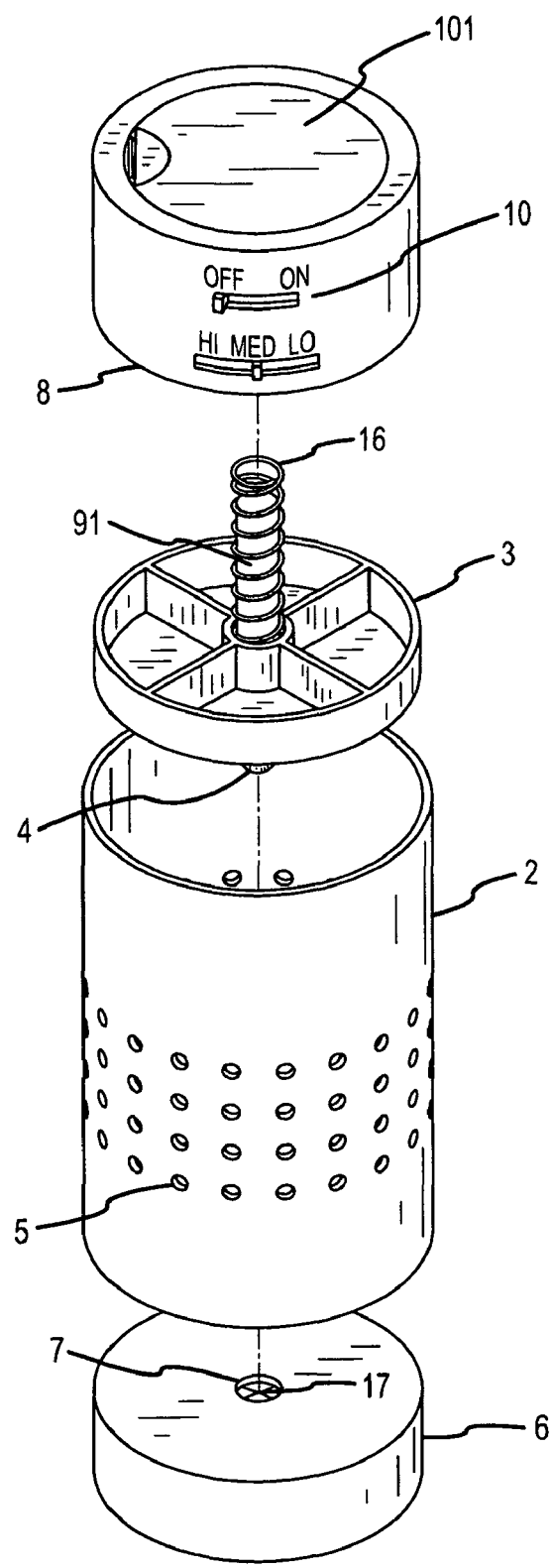
FIG. 7 shows an exploded view of one embodiment of the vapor-dispersing device of the present invention.
Figure 10:
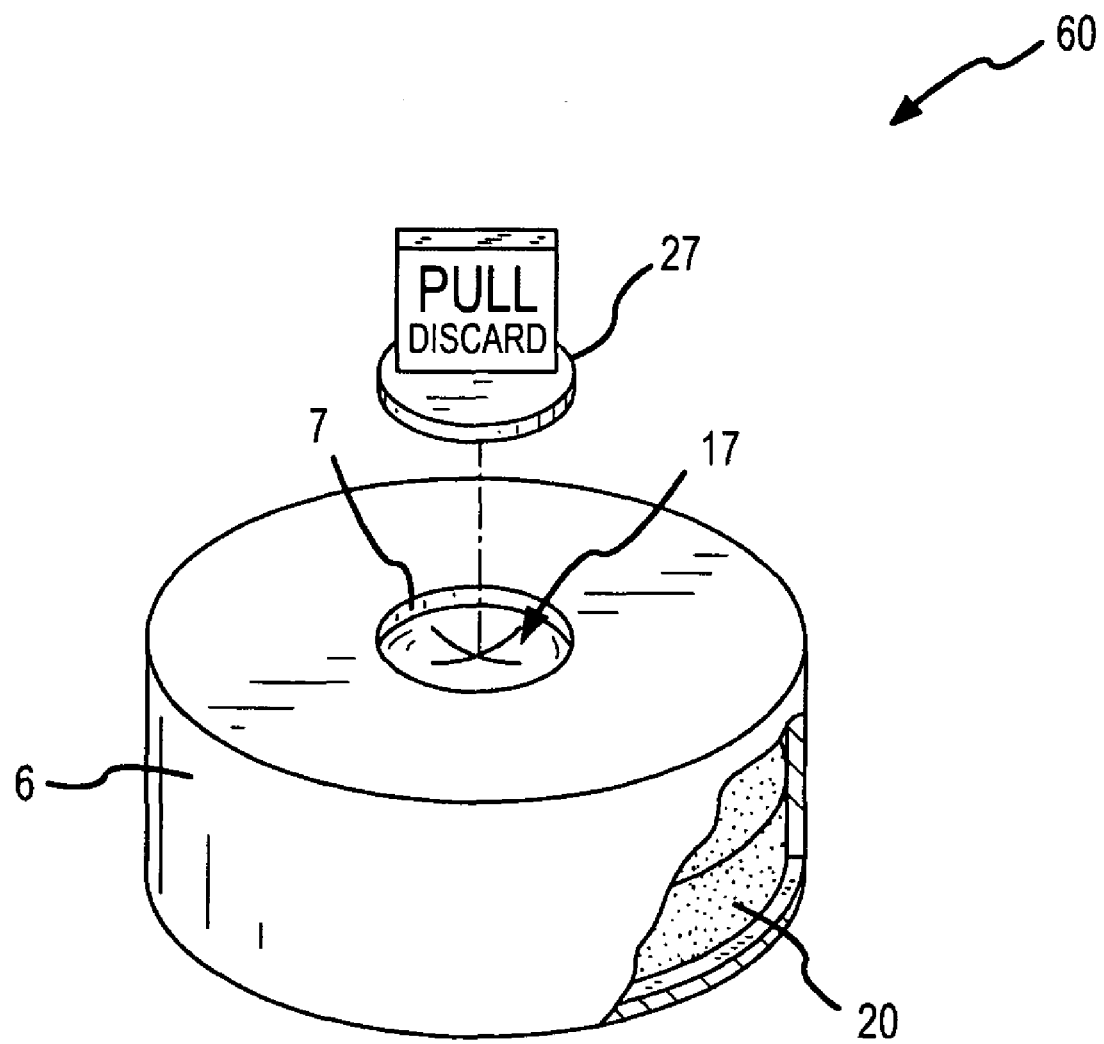
FIG. 10 shows one embodiment of an article of manufacture that provided for a refill reservoir for use in the vapor-dispersing device of the present invention.

Still referring to FIG. 1 (and also to FIG. 10 for clarity), another essential element of the vapor-dispersing device of the present invention is the reservoir 6, containing the volatile liquid and having a breachable opening 7, positioned at one end of the housing 2 in the stroke path of the moveable piston 3. The reservoir 6 is dimensioned and constructed of materials suitable to hold the volatile liquid to be vaporized from the device. The preferred capacity of the reservoir is from about 1 to about 500 milliliters, and the reservoir is necessarily a container having top, bottom, sides and an interior volume. The preferred shape of the reservoir is disc shaped, with dimensions of from about 0.5 inches in diameter to about 4 inches in diameter and from about 0.5 inches in height to about 3 inches in height. The important factor to the size and shape of the reservoir 6 is that it fit within one end of the housing 2. Thus if the housing is cylindrical, then the preferred shape of the reservoir may be disc-shaped. As mentioned above, a convenient configuration for these components, and one that simplifies assembly of the device is to use a cardboard, metal or plastic tube for the housing 2 and to press-fit a disc-shaped reservoir 6 into one end of the tube such that the bottom of the reservoir becomes the bottom of the housing and the bottom of the device itself. Such a configuration also allows for the reservoir 6 to be removable and replaceable by the user. As illustrated in FIGS. 7 and 10, and described in more detail below, the preferred configuration is for the reservoir 6, (containing the volatile liquid and a seal for shipping and storage), to be merchandised as a refill for the device of the present invention and for the user to place it within the housing. Placement of the reservoir into the housing will necessarily place the breachable opening of the reservoir into registry with the porous member of the piston.

The preferred materials of construction for the reservoir 6 are polyethylene, polypropylene, polyvinyl chloride (PVC) or glass, with the material chosen on the basis of cost, manufacturability and compatibility with the volatile material. Injection molding, blow-molding or thermoforming processes may be used to form the reservoir. The reservoir may be one-piece blow-molded, injection-molded, or simple molded construction or may be two or more pieces that are assembled to make the complete reservoir. For example, the reservoir may be comprised of a small disc-shaped container with sidewalls and a bottom defining a capacity of from about 10 mL to about 250 mL, having a separate lid that may be snapped, glued or sonically welded onto the sidewalls of the container to complete the reservoir. The reservoir necessarily has a top, a bottom and sides defining an interior capacity, and as mentioned above is preferentially disc-shaped.

A breachable opening 7 is configured on the one face of the reservoir 6. The opening may be created from the blow-pin in a blow molding operation, or may be molded into a glass reservoir, or into an injection molded top cover of the reservoir or drilled in during a later operation. This opening is preferably a small round hole, but regardless of the shape it should be complementary to the shape of the porous member that will repeatedly insert through it with each piston stroke. Thus, if the porous member 4 were preferably rod-shaped, the opening 7 on the reservoir 6 would preferably be round. To complement the preferred sizes/shapes of the porous member 4, the opening 7 may be from about 0.125 to about 1 inch in diameter (if round to accommodate a rod-shaped porous member) or about this general size if the opening is configured to some other shape such as square, rectangular or triangular. Regardless of the shape of the opening 7 on the reservoir, it is expected that the opening will take up from about 0.000156 to about 1 square inch of surface area. Furthermore the breachable opening 7 may further include a valve, pressed into the opening that can open when the porous protuberance pushes into and through it, and can re-close when the porous member is retracted from it. Such a valve may be an elastomeric polymer valve comprised of resilient polymer and consisting of slits that define flaps that open and close in response to breach from the porous member. Closing the opening 7 off with a flexible valve or other suitable rubber, synthetic polymer or silicone seal that retains its shape, may allow for the device to operate upside-down relative to FIGS. 1-3, or virtually in any other position, without the fear of leaking. In the preferred configuration for the device, the reservoir is at one end of the housing and the opening 7 of the reservoir is in registry with the porous protuberance on the piston. That is, the opening 7 and the porous member 4 on the piston should be coaxially aligned when the reservoir is positioned in the housing of the device.

Figure 2:
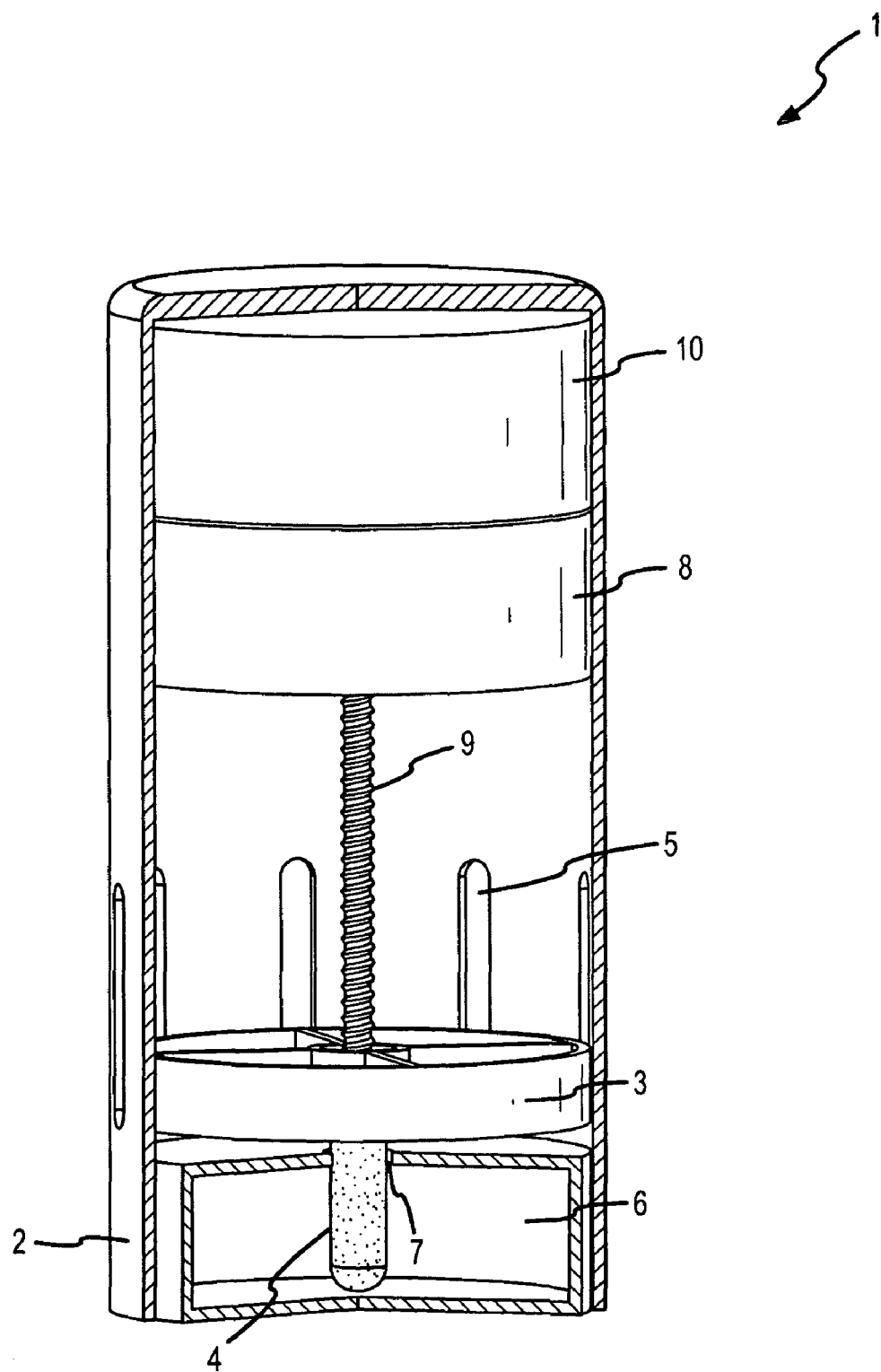
FIG. 2 conceptually outlines another embodiment of the vapor-dispersing device with moveable piston in a second position.
Figure 3:
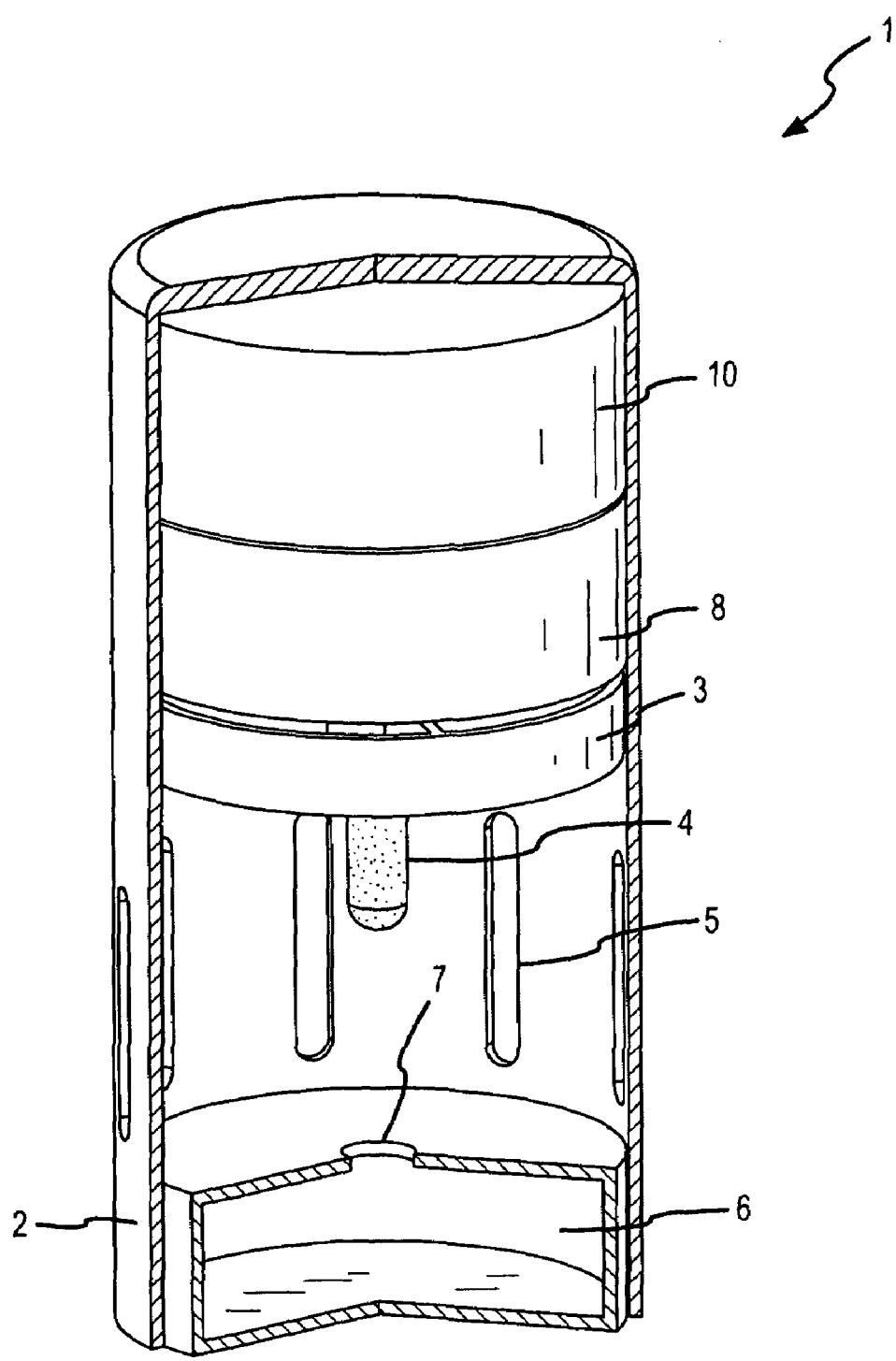
FIG. 3 conceptually outlines another embodiment of the vapor-dispersing device with moveable piston in a third position.

Referring now to FIGS. 2 and 3, one embodiment of the vapor-dispersing device of the present invention is shown with the piston 3 at each of two extreme first and second positions of a stroke length, respectively. FIG. 2 shows the moveable piston at an extreme first/lower position wherein the porous member 4 on the piston 3 is positioned through the opening 7 on the reservoir 6 and wherein the porous member 4 rests at the bottom of the reservoir 6, i.e., fully dipped into the reservoir. FIG. 3 shows the moveable piston 3 at a second/upper extreme position where the porous member 4 is fully retracted from the reservoir 6. Essential to the working of the present invention is that the piston 3 move in a stroke length defined somewhere between these extreme first/lower and second/upper positions depicted in FIGS. 2 and 3 respectively, such that each stroke of the piston 3 effectively dips the porous member 4 to some degree into the reservoir 6. Furthermore, each stroke of the piston 3 moves the porous member 4 past the vent or vents 5, and each down stroke pushes air out through the vent(s) 5 and each upstroke pulls ambient air back in through the vent(s) 5, wherein the piston functions as a bellows-means. The stroke of the piston 3 is the length measured between the first/lower and second/upper ends of the stroke, chosen somewhere between or equal to the extreme first/lower and second/upper positions of the piston shown in FIGS. 2 and 3. These upper and lower ends of the stroke are where the piston stops and reverses direction. This stroke length is minimally about the same length as the porous member 4 protruding from the piston 3, although the stroke length may be less than the length of the protruding porous member if the porous member is to remain at least partially in the reservoir at all times. The stroke length of the piston may be set such that the porous member 4 fully pulls out of the reservoir 6 or only partially pulls out of the reservoir upon each stroke. Setting a stroke length such that the porous member does not fully pull out of the breachable opening has the advantage that a better seal can be maintained around the porous member (described below) during operation of the device, (i.e., during the repeated strokes of the piston until the reservoir is empty). The stroke length may be determined in design and construction by the relative sizes of the parts, especially the drive means (described below), and/or may be automatically changed during operation of the device, or adjusted by the user. For example, a first stroke length upon turning on the device may be longer so that the porous member 4 pushes through and breaks a seal across the opening 7 on reservoir 6, but then the device automatically shortens the piston stroke after that first stroke to a length that maintains the porous member 4 at least to some degree within the reservoir 6. It is preferred that one extreme position of the piston stroke be such that the porous member 4 is pushed to the bottom of the reservoir 6. This preferred extreme position of the stroke ensures that the porous member pulls out all of the liquid in the reservoir, emptying it completely. The opposite extreme position of the stroke length is less important, and may be such that the porous member 4 is fully retracted or only partially retracted from the reservoir 6. The stroke length will define the degree to which the porous member 4 is exposed from the reservoir 6 and will affect the amount of the bellows-effect and the evaporation rate in general. That being said, it is preferable to have a stroke length for the piston 3 from about 0.125 inches to about 7 inches and this stroke length may be permanently fixed or may be variable throughout the dispensing of the volatile liquid in the device.

The frequency of the piston stroking has a direct effect on the evaporation of the volatile liquid and may be set at a very wide range of frequencies. For example, the piston may move very rapidly, almost like a vibration, with short fast strokes possible though a solenoid arrangement or rapid motor rotation. Or, in another embodiment, the piston may move very slowly with long slow strokes made possible by a motor and tooth-gear arrangement (described below). Depending upon the end-use, (air freshener, or insecticide), the size of the area to be treated, the amount of volatile liquid within the reservoir and how volatile the liquid is, the frequency of the piston strokes is preferably from about 1 stroke/hour to about 120 strokes/minute.

Figure 4:
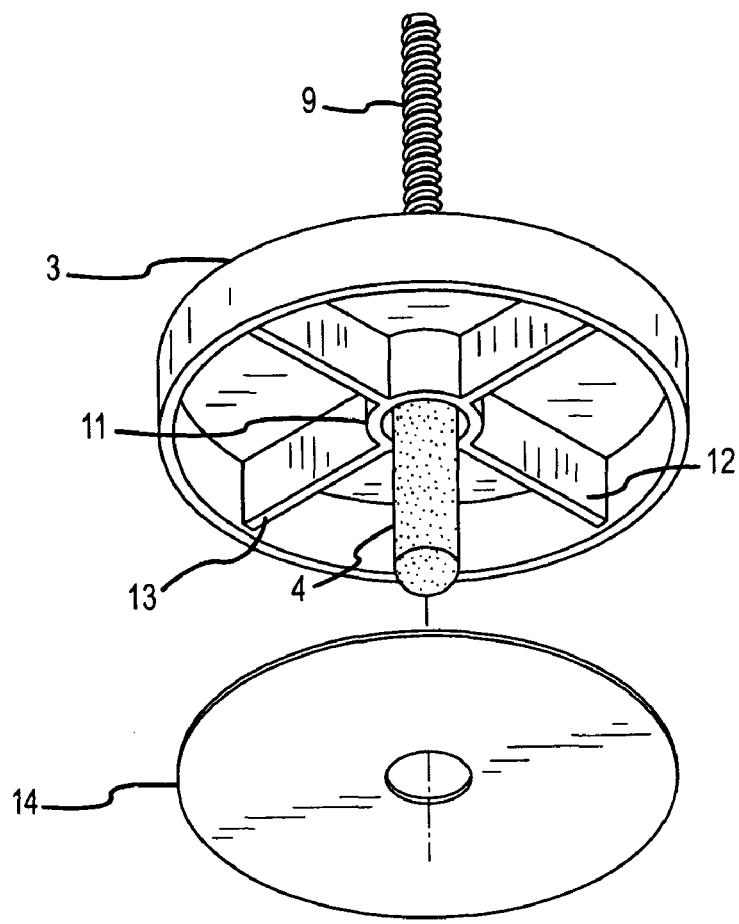
FIG. 4 shows an exploded view of one embodiment of the moveable piston of the vapor-dispersing device having optional evaporative pad.
Figure 5:
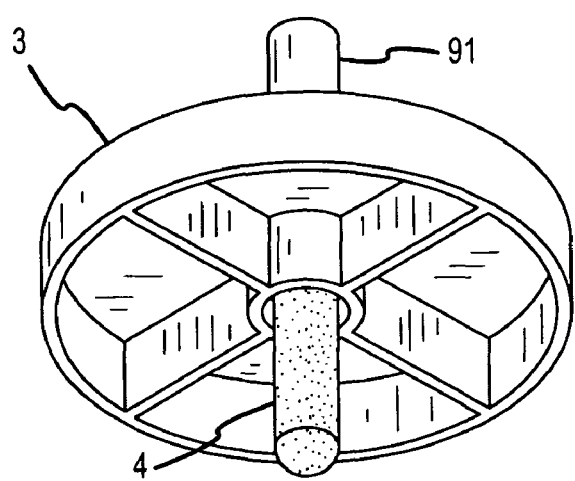
FIG. 5 shows another embodiment of the moveable piston of the vapor-dispersing device having a metal pin as the drive means.

FIGS. 4 and 5 depict two preferred embodiments of the piston 3. As mentioned above and now shown in greater detail in FIG. 4, it is preferable to have an injection molded disc-shaped plastic part as the piston 3 in the present invention. It is preferred that the piston 3 further comprises a recess or hole 11 molded in or post-drilled into either the top or the bottom to accommodate the porous member 4. Furthermore, the piston 3 preferably has support ribs 12, each having upper edges 13 defining a recessed shelf, and for the top and bottom of the piston to be identical (the part symmetrical across a plane slicing though the sidewall). The support ribs may then be used to support a solid doughnut shape piece (as mentioned earlier) to close off the spokes of the piston with a solid faceplate to ensure that it will move air during each stroke. Additionally, the support ribs 12 shown in FIG. 4 may be used to support a porous pad that can supplement the porous member 4 as the evaporation medium for the volatile liquid. In this way a pad can be placed on the piston in liquid communication with the porous member 4 to increase the evaporative surface area of the porous member 4. For the configuration shown in FIG. 4, it is preferable to use a doughnut-shaped pad 14 fitted over the porous member 4 and against the support ribs 12. In this manner, the porous pad 14 will rest on the edges 13 of the ribs 12 and will be in contact with the porous member 4. When the optional pad 14 is incorporated on the piston 3, the piston will necessarily have a closed off surface and therefore no additional faceplate as mentioned earlier is needed on the piston. The piston with the optional pad 14 will move the air upon each stroke since the pad 14 will provide for the preferred closed surface on the piston. Also shown in FIG. 4 is the drive means 9 that is used to connect the piston 3 to the electromechanical means (explained below). In this embodiment of the piston of the present invention shown in FIG. 4, the drive means 9 is a screw-gear, but may also be a cam rod or a flat-toothed gear that will drive the piston. Drive means 9 may be pressed into a hole or appropriately shaped recess provided on either the top or bottom of the piston 3 opposite porous member 4 (such a hole is on top of the part in FIG. 4 and thus not in view).

Referring again to FIG. 4, the pad 14 is an optional component in the device of the present invention. The use of the pad depends on the volatility of the liquid, the evaporation rate desired, the level of intensity of the vapor desired in the external environment around the device, and the application, (e.g., fragrance disperser or insecticide). For example, the pad 14 may increase the evaporation rate of a fragrance and cause a perceivable increase in the fragrance intensity delivered from the device when compared to a device without a pad 14. The pad 14 extends the evaporative surface of the porous member. The pad may be any size and shape that can reasonably fit onto the same side of the piston that carries the porous member. The preferred shape for the pad is doughnut shape, with the hole in the middle of the pad configured to about the same size as the diameter of the porous member so that there is a snug fit and liquid communication between the two for capillary flow to be possible. The pad may be any absorptive material such as cellulose, wood, or even a ceramic or porous plastic wafer. Most preferred is to construct pad 14 from $\frac{1}{16}$ to $\frac{1}{4}$ inch thick wet-laid pulp, for example AC-16 supplied by Filter Materials. This material is easily die-cut into discs or doughnuts and the scrap may be recycled into pulp so that there is no waste. Sheet stock of porous plastic, for example from $\frac{1}{16}$ to $\frac{1}{4}$ inch thick, may also be die-cut except that the waste is not recyclable. In certain applications such as insecticide delivery, the pad may be pre-treated with other materials, for example even with adhesives for the added benefit of trapping insects.

FIG. 5 is another preferred embodiment of the piston 3, with drive means 91 comprised of the metal pin from a solenoid. It is preferred to have such a drive means pressed into a recess or hole provided for on the top or bottom of the piston, opposite to the porous member 4. Most preferred is to mold a single hole completely through the center of the plastic piston and to press the porous member and the solenoid pin into that same hole from opposite directions until they meet in the middle. When the porous member 4 and the solenoid pin 91 have identical diameters, the assembly of the piston is greatly simplified and the cost is substantially reduced. The piston 3 may be molded in the shape of a plastic wheel, with the ribs 12 forming the spokes and the central hole 11 forming the hub of the wheel, and that hub may used as the receptacle for both the porous member and the solenoid pin pressed in from opposite directions to resemble axles on a wheel. To ensure the piston will move air, a plastic disc with a central hole (i.e., a doughnut shaped flat piece of relatively firm material such as plastic, wood or fiberboard) may be fixedly attached onto either the top or the bottom of the piston, for example with glue.

Figure 6:
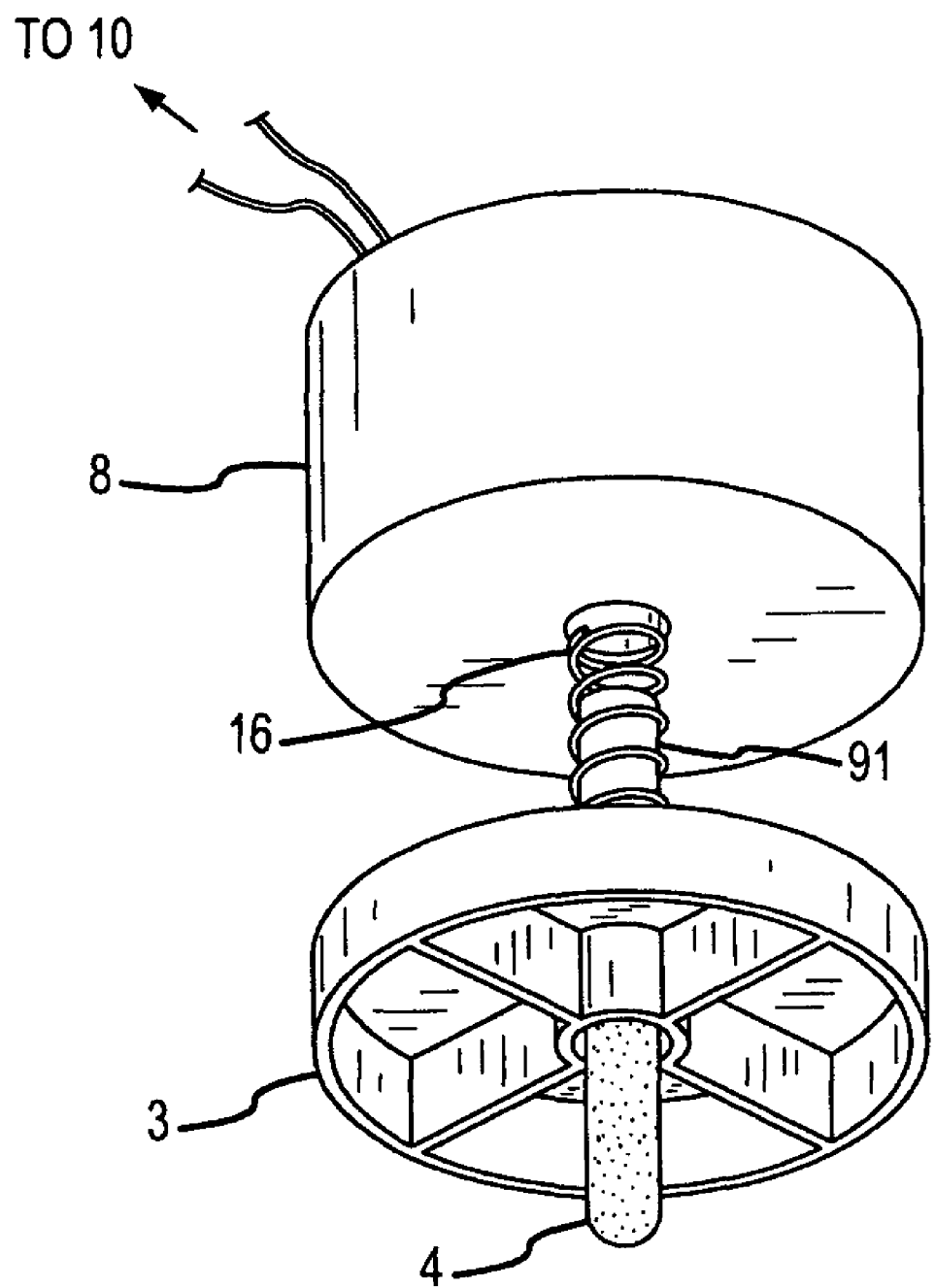
FIG. 6 shows a preferred embodiment of the electromechanical means, drive means and movable piston, wherein the electromechanical means together with the drive means comprise a solenoid, the metal solenoid pin and the solenoid return spring.

FIG. 6 details one configuration for a subassembly comprising the piston, the electromechanical means, and the drive means for incorporation into the device of the present invention. As mentioned above, one preferred embodiment is to move the piston with a solenoid, and for that preferred embodiment the drive means that connects the piston to the electromechanical means is preferably the metal pin of the solenoid and the electromechanical means is the remainder of the solenoid (the magnetic coil windings, housing, etc., less the pin). As shown in FIG. 6, piston 3 may be fitted with both porous member 4 and solenoid pin 91. Fitted on the solenoid pin 91 is preferably the solenoid return spring 16. The solenoid 8, along with pin 91 and return spring 16, is designed to move piston 3 in repetitive strokes by intermittently powering the solenoid 8 with electrical control means 10. For example, electromechanical means 8 preferably comprises a pull-type solenoid that operates to pull up to its upper position upon supply of power to the solenoid. The piston then returns back down to a lower position at least partly in the reservoir by the force of the return spring 16 when the power is cut to the solenoid. Depending on the frequency of voltage pulses sent to the solenoid 8 from the electrical control means 10, the piston will move up and down to a particular frequency that is preferably from about 1 stroke per hour to about 120 strokes per minute. An audible "clicking" sound may emanate from the device of the present invention when configuring the device with a solenoid, and this sound may provide a unique audible cue to the consumer that the device is powered and working properly. A clicking noise when the device is in operation may be due to the metal pin hitting the inside of the solenoid body upon activation of the solenoid. The electric control means 10 may be comprised of a simple circuit to supply rectified DC voltage from an AC plug, and may feature an "on-off" switch (described below).

FIG. 7 delineates a preferred embodiment of the present invention in exploded view wherein the electromechanical means comprises a solenoid 8, the drive means comprises the metal pin 91 and return spring 16 of the solenoid, along with an electrical control means 10 further comprising on/off and "high/low" switches and a battery compartment door 101. For this preferred configuration of the device, the piston 3, in the preferred shape of a plastic wheel, further comprises the porous member 4 and solenoid pin 91 pressed in from opposite directions into the top and bottom of the piston. The preferred embodiment shown in FIG. 7 also features the preferred configuration for the housing 2, wherein the housing is comprised of a tube (that forms the sidewalls of the device), the top of the electric control means 10 forming the top of the housing, and the bottom of the reservoir 6 forming the bottom of the housing when these parts are assembled. This embodiment represents a very cost effective configuration for the device of the present invention, wherein the reservoir 6 and the electrical control means 10 are pressed into the top and bottom openings of a cylindrical tube 2 to form the overall shape and outer walls of the assembled device. Also shown in FIG. 7 is a resealable valve 17 pressed into the opening 7 of reservoir 6, and the vents 5 on the housing 2 configured as many small holes. As mentioned, resealable valve 17 may be a plastic polymeric valve such as an elastomeric valve that has slits that remain closed and sealed until the piston penetrates the valve. The valve can be the elastomeric type used in many squeezable shampoo and soap containers. It may be rubber or silicone polymer. Alternatively, or in addition to the resealable valve 17, there may be a seal over the opening of the reservoir (or over the valve if it is used) such that the device can be merchandized without fear of leakage from the reservoir. For example, a foil or shrink-wrap plastic can cover the reservoir opening when the device is merchandised. It may be preferable to have a foil seal that is simply broken open by the first down-stroke of the piston, thereby eliminating the need to the consumer to peel away a seal prior to use of the device.

Figure 8:
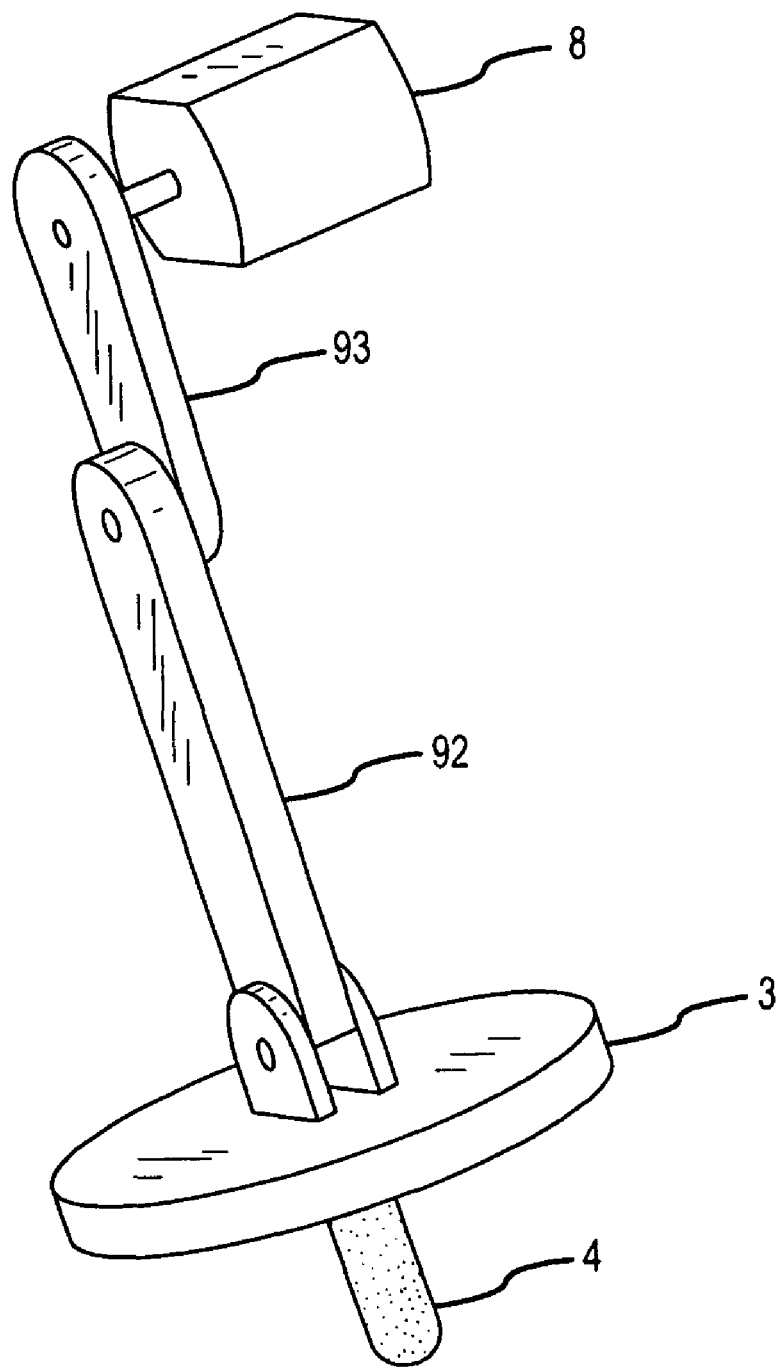
FIG. 8 shows one embodiment of the electromechanical means, the drive means and moveable piston of the vapor-dispersing device.
Figure 9:
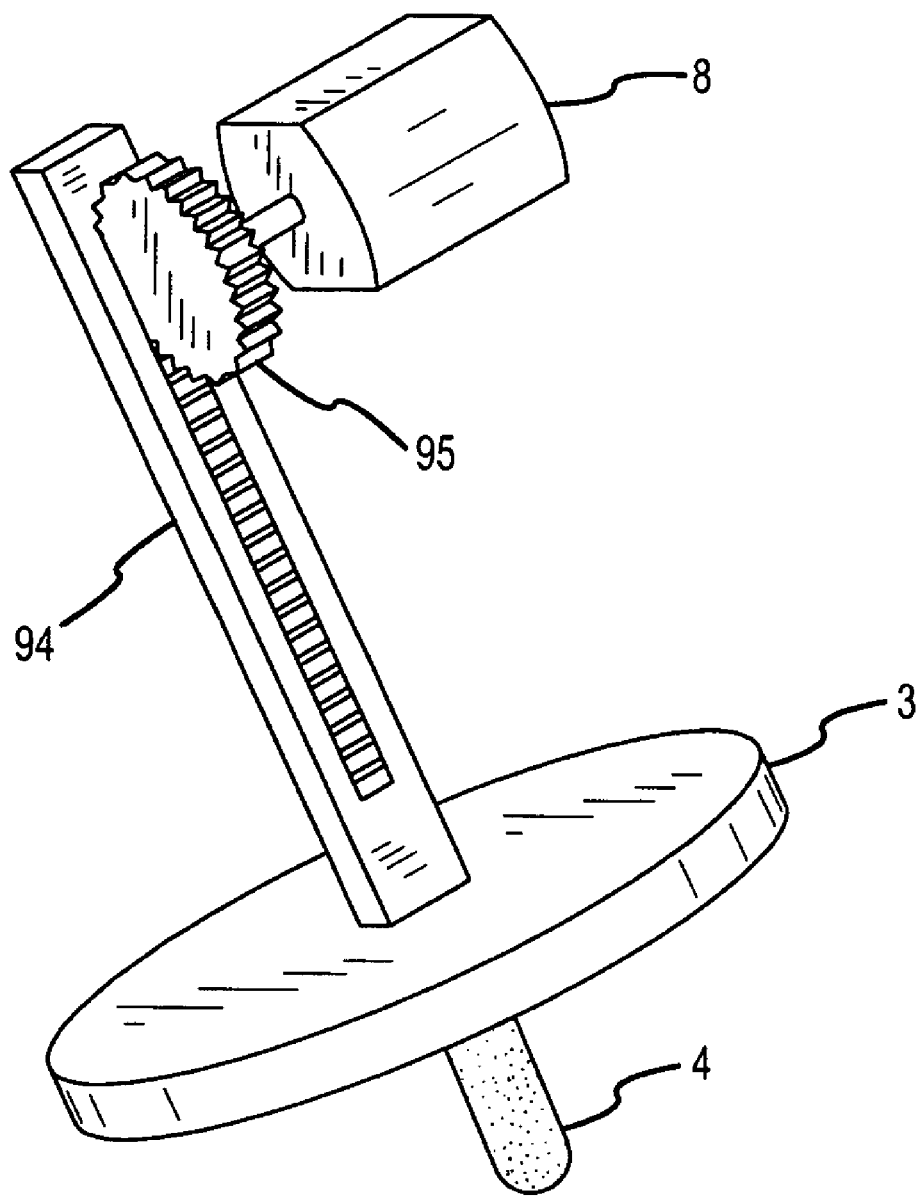
FIG. 9 shows another embodiment of the electrochemical means, the drive means and moveable piston of the vapor-dispersing device.

Referring now to FIG. 8, another embodiment of the drive means of the present invention is shown. In this configuration, the piston 3 and attached porous member 4 are moveable in a stroke path through the concerted motions possible from a hinged arm 92 movably fastened to the piston 3, and a rotating cam member 93 connected between the hinged arm 92 and the electromechanical means 8, which in this instance is preferably a simple motor. Similarly, as shown in FIG. 9, movement of the piston 3 is possible along a defined stroke path by incorporation of a toothed gear 94 fixedly attached to piston 3, wherein the piston is moved in an up and down stroking fashion through the reversible rotation of gear 95 driven by motor 8. In this embodiment, the motor 8 would reverse direction by reversing the polarity of the voltage from the electrical means 10 to the motor 8.

The electrical control means 10 shown conceptually in FIGS. 1, 2, 3 and 7 may be of vast configurations depending on the power source desired for the device (AC or DC battery) and the level of independent control intended for the end user, for example if it further comprises logic control. Minimally the electrical control means 10 supplies power to the electromechanical means. It may house at least one battery within a battery compartment or it may conduct AC power from an electrical outlet through electrical receptacle prongs protruding directly from the housing of the device or from an electrical cord running from the device. For example, the control means 10 may comprise a voltage supply and a switch, with internal electrical connection to the electromechanical means. In this way the electrical control means 10 may take AC house current (110 or 220 v) and route it directly into the electromechanical means via wires and/or contacts. The main control switch may include a simple ON/OFF switch, and/or the electrical control means may also include a multiple position switch for "HIGH-MED-LOW" settings that provides for selection of three electrical current levels. The multiple-position switch may incorporate a rheostat to adjust the output of the device through adjustment of the frequency of the piston strokes, or may control an integrated circuit to control the strokes of the piston by adjusting the frequency, duration and polarity of the electrical signals to the electromechanical means. The control means 10 may be much more elaborate, comprising a timer circuit, an integrated circuit and/or a programmable integrated circuit. The electrical control means may further comprise a gas sensor for detecting malodors or marker molecules, or a light, motion or sound sensor, for example for turning on the power in the device when the device senses odors, marker molecules, light, movement and/or sounds. The electrical control means may further include a digital display for logic control. The programmable IC may allow the user to operate the device at different intensity levels. The function of the integrated circuit is to control the voltage signals to the electromechanical means. Incorporating a gas sensor, or light, motion or sound sensor may allow the device to operate independently of user interaction, (i.e., the device becomes entirely automatic).

FIG. 10 illustrates a preferred configuration of the reservoir for use in the present invention. In this preferred embodiment, the reservoir 6 and a removable sealing member 27 become an article of manufacture 60 that may be merchandised as a refill for use in the device. In this way the user can change out reservoirs and keep the remainder of the device including the relatively more expensive electronics, for reuse. Various refills 60 may be marketed for use in the device of the present invention, for example many different fragrance varieties or different insecticidal refills for use against specific household and outdoor pests. As mentioned earlier, it is preferred to seal the reservoir 6 with a small sealing member such as a pullout plug 27 that fits snugly into the opening 7 of the reservoir, or to use some other seal or covering over the opening. In this particular embodiment, the plug 27 seals the reservoir 6 and protects the valve 17 from leakage or drying out during the time the reservoir is merchandised and sitting on store shelves or in warehouses. Alternatively the reservoir with volatile liquid 20 inside may be shrink-wrapped with plastic film. In this way, the consumer may purchase the described article of manufacture 60, pull out the disposable plug 27 or peel away a foil seal or remove a shrink-wrapped film, and then insert the reservoir into the end of the housing where the opening 7 will be in registry with the porous member. When the reservoir is emptied of the volatile liquid 20, the user may pull it out from the housing and replace it with a fresh one. Most preferred is to incorporate a viewing window on the housing of the device along with a clear or semi-transparent reservoir such that the consumer can easily see the level of volatile liquid remaining in the device and to know when to remove and replace the reservoir.

The volatile material 20 in the reservoir for evaporation from the device of the present invention may be present from about 0.1 gram to about 500 gram. Depending on whether the composition is a fragrance or an insecticide, the composition may contain anywhere from trace actives to 100% actives and may contain any number and amount of solvents and/or carriers, volatile or otherwise. For example, the device of the present invention may comprise a volatile material further consisting of only a single volatile chemical such as citronella. In another embodiment of the invention the volatile material may comprise only eucalyptus oil. The material may comprise anywhere from one or a few to up to many active materials dissolved or compounded with solvents and carriers that may or may not be volatile. Most preferred is to utilize volatile mixtures (comprising mixtures of actives and solvents together) wherein all of the components are volatile such that the reservoir will eventually be empty of any visible contents after use-up.

For use as a fragrancing device, the fragrance components of the volatile material in the present invention may comprise one of more volatile organic compounds available from any of the now known, or hereafter established, perfumery suppliers, such as International Flavors and Fragrances (IFF) of New Jersey, Givaudan of New Jersey, Firmenich of New Jersey, etc. Many types of fragrances can be used in the present invention. Preferably the fragrance materials are volatile essential oils. The fragrances, however, may be synthetically derived materials (aldehydes, ketones, esters, etc.), naturally derived oils, or mixtures thereof. Naturally derived fragrance substances include, but are not limited to, musk, civet, ambergis, castoreum and like animal perfumes; abies oil, ajowan oil, almond oil, ambrette seed absolute, angelic root oil, anise oil, basil oil, bay oil, benzoin resinoid, bergamot oil, birch oil, bois de rose oil, broom abs., cajeput oil, cananga oil, capsicum oil, caraway oil, cardamon oil, carrot seed oil, cassia oil, cedar leaf, cedarwood oil, celery seed oil, cinnamon bark oil, citronella oil, clary sage oil, clove oil, cognac oil, coriander oil, cubeb oil, cumin oil, camphor oil, dill oil, estragon oil, eucalyptus oil, fennel sweet oil, galbanum res., garlic oil, geranium oil, ginger oil, grapefruit oil, hop oil, hyacinth abs., jasmin abs., juniper berry oil, labdanum res., lavander oil, laurel leaf oil, lavender oil, lemon oil, lemongrass oil, lime oil, lovage oil, mace oil, mandarin oil, mimosa abs., myrrh abs., mustard oil, narcissus abs., neroli bigarade oil, nutmeg oil, oakmoss abs., olibanum res., onion oil, opoponax res., orange oil, orange flower oil, origanum, orris concrete, pepper oil, peppermint oil, peru balsam, petitgrain oil, pine needle oil, rose abs., rose oil, rosemary oil, sandalwood oil, sage oil, spearmint oil, styrax oil, thyme oil, tolu balsam, tonka beans abs., tuberose abs., turpentine oil, vanilla beans abs., vetiver oil, violet leaf abs., ylang ylang oil and like vegetable oils, etc. Synthetic fragrance materials include but are not limited to pinene, limonene and like hydrocarbons; 3,3,5-trimethylcyclohexanol, linalool, geraniol, nerol, citronellol, menthol, borneol, borneyl methoxy cyclohexanol, benzyl alcohol, anise alcohol, cinnamyl alcohol, β-phenyl ethyl alcohol, cis-3-hexenol, terpineol and like alcohols; anethole, musk xylol, isoeugenol, methyl eugenol and like phenols; α-amylcinnamic aldehyde, anisaldehyde, n-butyl aldehyde, cumin aldehyde, cyclamen aldehyde, decanal, isobutyl aldehyde, hexyl aldehyde, heptyl aldehyde, n-nonyl aldehyde, nonadienol, citral, citronellal, hydroxycitronellal, benzaldehyde, methyl nonyl acetaldehyde, cinnamic aldehyde, dodecanol, α-hyxylcinnamic aldehyde, undecenal, heliotropin, vanillin, ethyl vanillin and like aldehydes; methyl amyl ketone, methyl β-naphthyl ketone, methyl nonyl ketone, musk ketone, diacetyl, acetyl propionyl, acetyl butyryl, carvone, menthone, camphor, acetophenone, p-methyl acetophenone, ionone, methyl ionone and like ketones; amyl butyrolactone, diphenyl oxide, methyl phenyl glycidate, .gamma.-nonyl lactone, coumarin, cineole, ethyl methyl phenyl glicydate and like lactones or oxides; methyl formate, isopropyl formate, linalyl formate, ethyl acetate, octyl acetate, methyl acetate, benzyl acetate, cinnamyl acetate, butyl propionate, isoamyl acetate, isopropyl isobutyrate, geranyl isovalerate, allyl capronate, butyl heptylate, octyl caprylate octyl, methyl heptynecarboxylate, methine octynecarboxylate, isoacyl caprylate, methyl laurate, ethyl myristate, methyl myristate, ethyl benzoate, benzyl benzoate, methylcarbinylphenyl acetate, isobutyl phenylacetate, methyl cinnamate, cinnamyl cinnamate, methyl salicylate, ethyl anisate, methyl anthranilate, ethyl pyruvate, ethyl α-butyl butylate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl isovalerate, isobornyl acetate, linalyl acetate, methyl anthranilate, methyl dihydrojasmonate, nopyl acetate, β-phenylethyl acetate, trichloromethylphenyl carbinyl acetate, terpinyl acetate, vetiveryl acetate and like esters, and the like. Suitable fragrance mixtures may produce a number of overall fragrance type perceptions including but not limited to, fruity, musk, floral, herbaceous (including mint), and woody, or perceptions that are in-between (fruity-floral for example). Typically these fragrance mixtures are compounded by mixing a variety of these active fragrance materials along with various solvents to adjust cost, evaporation rates, hedonics and intensity of perception. Well known in the fragrance industry is to dilute essential fragrance oil blends (natural and/or synthetic) with solvents such as ethanol, isopropanol, hydrocarbons, acetone, glycols, glycol ethers, water, and combinations thereof, and using solvent up to as much as 90% of the volatile fragrance composition. Thus a preferred fragrance composition for use as the volatile composition in the present invention is comprised of a mixture of many fragrance actives and volatile solvents, sometimes along with smaller amounts of emulsifiers, stabilizers, wetting agents and preservatives. More often than not, the compositions of the fragrance mixtures purchasable from the various fragrance supply houses remain proprietary.

Volatile insecticide compositions for use in the present invention are those of the type described in U.S. Pat. No. 4,663,315 (to Hasegawa, et al.) and incorporated herein by reference. Hasegawa describes many useful volatile insecticidal compositions that will work well within the reservoir of the present invention.

The volatile material for use in the present invention has been described as a liquid, however it is important to realize that any range of viscosities may be used for this liquid. For example, the material placed into the reservoir for evaporation may be a thin liquid, a thickened gel, an emulsion or suspension, or a very viscous liquid, for example resembling a gel or a waxy semi-solid. Using a volatile liquid with substantially high viscosity has the advantage that the device may be held and operated in a variety of positions (even upside-down) without fear of leaking or dripping from the opening of the reservoir.

We have herein described a unique and heretofore unknown vapor-dispensing device and vapor-dispersing method that comprises a moving piston in the absence of heating elements or building pressure. The device operates at ambient temperature and pressure and evaporates the contents of a reservoir through the repeated dipping of a porous member in and out of the material to be evaporated. The moving piston provides for air movement to assist in moving the vapors out from the unit and may also provide a noise such as a clicking sound to indicate to the consumer that the unit is operating. This invention will find use as an air freshener and an insecticidal device.

We claim:
1. A vapor dispersing device comprising:
  a. a housing with top, bottom, side walls and an interior;
  b. a vent on said housing allowing air flow between said interior and the environment exterior to said housing;
  c. a piston moveable along a path between first and second positions within said housing, said piston comprising a top, bottom and sidewalls;
  d. a porous wick member protruding from the bottom of said piston;
  e. a reservoir positioned within said housing having an opening in registration with said porous wick member;
  f. a volatile liquid contained within said reservoir;
  g. a drive means connected to said piston opposite said porous wick member for repeatedly dipping said porous wick member into said reservoir through said opening;
  h. an electromechanical means connected to said drive means for electromechanically moving said piston along said path within said housing through said drive means; and,
  i. an electrical control means for powering and electronically controlling said electromechanical means.

2. The vapor dispersing device of claim 1, wherein said porous wick member is selected from the group consisting of porous plastic, ceramic, graphite and fiber.

3. The vapor-dispersing device of claim 1, wherein said opening is fitted with a resealable valve.

4. The vapor-dispersing device of claim 3, wherein said resealable valve is a cross-slit silicone elastomeric valve.

5. The vapor dispersing device of claim 1, wherein said opening is initially sealed closed with a breakable or removable foil.

6. The vapor dispersing device of claim 1, wherein said electromechanical means is an AC or DC electrical motor.

7. The vapor dispersing device of claim 6, wherein said drive means further comprises at least one toothed gear.

8. The vapor dispersing device of claim 6, wherein said drive means further comprises a hinged arm and rotating cam connected between said motor and said piston.

9. The vapor-dispersing device of claim 1, wherein said electromechanical means is selected from the group consisting of a push-type solenoid, pull-type solenoid, and a push/pull-type solenoid.

10. The vapor-dispersing device of claim 9, wherein said drive means consists of a metal pin surrounded by a spring, wherein said pin is attached to said piston opposite said porous wick member.

11. The vapor dispersing device of claim 1, wherein said electrical control means further includes an electrical cord terminating in a plug having suitable prong configuration for connection to a 110 volt or 220 volt electrical outlet.

12. The vapor dispersing device of claim 1, wherein said electrical control means further includes electrical prongs protruding directly from said housing for plugging said device directly into a 120 volt or 220 volt electrical outlet for both support and electrical power.

13. The vapor dispersing device of claim 1, wherein said electrical control means further comprises a rectifier.

14. The vapor dispersing device of claim 1, wherein said electrical means further comprises at least one battery and a moveable door for accessing said battery.

15. The vapor dispersing device of claim 1, wherein said electrical means further comprises an ON/OFF switch.

16. The vapor dispersing device of claim 1, wherein said electrical means further comprises a timer circuit programmable by the user.

17. The vapor dispersing device of claim 1, wherein said electrical control means further comprises a logic circuit for programming run time and intensity output of the device.

18. The vapor-dispersing device of claim 1, wherein said volatile liquid is a blend of synthetic or natural fragrance oils and solvents.

19. The vapor-dispersing device of claim 1, wherein said volatile liquid is an insecticide mixture.

20. A method for dispensing vapor into the environment comprising the steps of:
   a. providing a vapor-dispersing device according to claim 1; and,
   b. interacting with said electrical control means to operate said device.

* * * * *